United States Patent
Sciutto Conde et al.

(10) Patent No.: US 11,020,449 B2
(45) Date of Patent: Jun. 1, 2021

(54) USE OF THE GK-1 PEPTIDE AS AN ANTITUMORAL AND/OR ANTIMETASTATIC AGENT

(71) Applicant: UNIVERSIDAD NACIONAL AUTÓNOMA DE MÉXICO, Mexico City (MX)

(72) Inventors: Edda Lydia Sciutto Conde, Morelos (MX); Gladis del Carmen Fragoso Gonzalez, Mexico City (MX); Diana Torres Garcia, Mexico City (MX); Jacquelynne Brenda Cervantes Torres, Mexico City (MX); Rene Alvaro Segura Velazquez, Mexico City (MX); Armando Perez Torres, Mexico City (MX); Karen Manucharyan, Mexico City (MX)

(73) Assignee: UNIVERSIDAD NACIONAL AUTÓNOMA DE MÉXICO, Mexico City (MX)

( * ) Notice: Subject to any disclaimer, the term of this patent is extended or adjusted under 35 U.S.C. 154(b) by 110 days.

(21) Appl. No.: 16/302,786

(22) PCT Filed: May 18, 2017

(86) PCT No.: PCT/MX2017/000055
§ 371 (c)(1),
(2) Date: Nov. 19, 2018

(87) PCT Pub. No.: WO2017/200369
PCT Pub. Date: Nov. 23, 2017

(65) Prior Publication Data
US 2020/0222495 A1   Jul. 16, 2020

(30) Foreign Application Priority Data

May 18, 2016   (MX) ................... MX/a/2016/006460

(51) Int. Cl.
*A61K 38/10* (2006.01)
*A61P 35/00* (2006.01)

(52) U.S. Cl.
CPC .............. *A61K 38/10* (2013.01); *A61P 35/00* (2018.01)

(58) Field of Classification Search
CPC ................................ A61K 38/10; A61P 35/00
See application file for complete search history.

(56) References Cited

U.S. PATENT DOCUMENTS

2014/0302085 A1 * 10/2014 Sciutto Conde ..... A61K 39/145
424/193.1

FOREIGN PATENT DOCUMENTS

| MX | PA05003413 A | 2/2007 |
| MX | 270782 | 10/2009 |
| WO | 2013015668 A2 | 1/2013 |

OTHER PUBLICATIONS

Gevorkian G., et al.; Immunodominant synthetic peptides of Taenia crassiceps in murine and human cysticercosis. Immunology Letters;1996; vol. 49, No. 3, pp. 185-189.
Segura-Velazquez R., et al., Clin Vaccine Immunol, 2009. 16(9): p. 1338-43.
Segura-Velazquez R., et al., Vaccine, 2006. 24(8): 1073-80.
Toledo A et al., Infection and Immun. 1999; 67 (5): 2522-30.
Gladis F, et al., Clinical and Vaccine Immunology 2011; 18(7):1067-1076.
Perez-Torres Armando et al.; The Synthetic Parasite-Derived Peptide GK1 Increases Survival in a Preclinical Mouse Melanoma Model; Cancer Biotherapy & Radiopharmaceuticals; Nov. 1, 2013; vol. 28, N° 9, pp. 682-690.
Perez-Torres Armando et al.; Hematological Effects, Serum, and Pulmonary Cytokine Profiles in a Melanoma Mouse Model Treated with GK1; Cancer Biotherapy & Radiopharmaceuticals Aug. 1, 2015, vol. 30, N° 6, pp. 247-254.
Pinon-Zarate Gabriela et al.; GK-1 Improves the Immune Response Induced by Bone Marrow Dendritic Cells Loaded with MAGE-AX in Mice with Melanoma; Journal of Immunology Research 2014. Nov. 30, 2013, Article No. 158980.
Vera-Aguilera Jesus et al. Novel Treatment of Melanoma: Combined Parasite-Derived Peptide GK-1 and Anti-Programmed Death Ligand 1 Therapy; Cancer Biotherapy & Radiopharmaceuticals Mar. 2017, vol. 32, N° 2, pp. 49-56.
International Search Report dated Aug. 11, 2017 issued in International Patent Application No. PCT/MX2017/000055.
Written Opinion dated Aug. 11, 2017 issued in International Patent Application No. PCT/MX2017/000055.

* cited by examiner

*Primary Examiner* — Sudhakar Katakam
(74) *Attorney, Agent, or Firm* — Shumaker, Loop & Kendrick, LLP

(57) ABSTRACT

The present invention refers to the use of the peptide defined by the amino acid sequence G-Y-Y-Y-P-S-D-P-N-T-F-Y-A-P-P-Y-S-A, named GK-1, to be used as an antitumor and antimetastatic agent or for the treatment of cancer, specifically of basal cell carcinoma, squamous cell carcinoma, transitional cell carcinoma, and adenocarcinoma, and preferably for the treatment of breast cancer.

9 Claims, 5 Drawing Sheets

Specification includes a Sequence Listing.

USE OF THE GK-1 PEPTIDE AS AN ANTITUMORAL AND/OR ANTIMETASTATIC AGENT

REFERENCE TO AN ELECTRONIC SEQUENCE LISTING

The contents of the electronic sequence listing (5309-17US_ST25.txt; Size: 1 KB; and Date of Creation: Aug. 16, 2019) is herein incorporated by reference in its entirety.

FIELD OF THE INVENTION

The present invention falls within the medical field, particularly oncology. It is related to the use of the GK-1 peptide as an antitumor and/or antimetastatic agent, as well as a cancer treatment.

BACKGROUND

According to the World Health Organization (WHO), 8.2 million neoplasia-related deaths were reported worldwide in 2012, and 14.1 million new cases were diagnosed on the same year [Stewart B. W. et al., World Health Organization. 2014; 1-953]. Neoplasms can be classified based on the type of organ or tissue and on the cell line from which they are originated. Depending on the cell type, neoplasms are classified as [Weber G. F., Molecular Mechanisms of Cancer. 2007; doi: 10.1007/978-1-4020-6016-8; 1-643]:
1. Carcinoma. It is formed from epithelial cells. Depending on their type, it has specific names:
   1.1 Adenocarcinoma. It arises from epithelial cells of glandular tissue.
   1.2 Basal cell carcinoma. It originates in the basal layer of the epidermis.
   1.3 Squamous cell carcinoma. It can develop from cells found in the upper layer of the epidermis, i.e. in the skin surface and in the lining of some organs [American Cancer Society, Basal and Squamous Cell Skin Cancers. American Cancer Society. Atlanta, Ga. 2016. Available in: http://www.cancer.org/acs/groups/cid/documents/webcontent/003139-pdf.pdf, retrieved on Apr. 26, 2016].
   1.4 Transitional cell carcinoma. Found in transitional epithelium.
2. Sarcoma. It arises in non-epithelial or connective tissue like bone, soft tissues, fatty tissue, fibrous tissue, blood vessels, and lymph vessels.
3. Leukemia. This type of cancer does not develop solid tumors, and it arises in the bone marrow.
4. Lymphoma. Cancer of lymph tissue. It is classified as:
   4.1 Hodgkin's lymphoma. It is characterized by the presence of Reed-Sternmerg cells, stemming from B cells.
   4.2 Non-Hodgkin's lymphoma. This cancer type can arise from B as well as from T cells.
5. Multiple myeloma. Also known as Kahler's disease, this neoplasm develops from abnormal plasmatic cells, called myeloma cells, which are capable of forming bone tumors.
6. Germinal cell tumors. They originate from sperm cells or ova.
7. Neuroendocrine tumors. They develop from hormone-secreting cells, like carcinoid tumors, usually found in the gastrointestinal tract.
8. Melanoma. Malignant proliferation of melanocytes; these cells produce melanin, which is a pigment found in skin, eyes, and hair. Most melanomas develop on the skin, but they can arise in mucous membranes of the mouth, nose, and anus, among others [Weber G. F. Molecular Mechanisms of Cancer. 2007; DOI: 10.1007/978-1-4020-6016-8; 1-654].

Among the different types of cancer, the breast cancer is the most prevalent type of neoplasia, and it is the leading cause of death in women worldwide [Stewart B. W. et al., World Health Organization. 2014; 1-953]. Although the breast cancer occurs more frequently in women, men are not exempt; according to the American Cancer Society (ACS), male breast cancer incidence has increased by 0.8% annually since 1975. Currently, incidence of male breast cancer in the United States is about 1% of the total cases, which makes difficult to assess etiologic factors for this group. The African American proportion of the U.S. population as well as the elderly people (over 50 years old) are the people with most risk of developing breast cancer. [American Cancer Society. Breast Cancer Facts & Figures 2015-2016. Breast cancer facts & figures, 2015: p. 1-44. Available in: http://www.cancer.org/acs/groups/content/@research/documents/document/acspc-046381.pdf, retrieved Apr. 26, 2016]. Based on the above, the breast cancer is a major public health problem worldwide.

Among the most widely used cancer treatments are the immunotherapies like, IFN-α, IL-2, IL-15, IL-21, anti-CD25, anti-PD-1, and anti-CTLA-4, among others [American Cancer Society. Cancer Immunotherapy, 2015 Nov. 5, 2015: p. 1-19; Roberti M P, et al., Breast Cancer Res Treat. 2012; 136(3):659-71; Rech A J, et al., Ann N Y Acad Sci. 2009; 1174:99-106; Vonderheide R H, et al., Clin Cancer Res. 2010; 16(13):3485-94]. However, these therapies can cause adverse effects such as diarrhea, fatigue, dermatitis, and follicular eruption [Lim J L, et al., J. Am Acad Dermatol. 2008;59 (2 Suppl 1):S60-1; Vonderheide R H, et al., Clin Cancer Res. 2010; 16(13):3485-94; Jaber S H, et al., Arch Dermatol. 2006; 142(2):166-72. doi: 10.1001/archderm.142.2.166], as well as an increased risk of develop autoimmune diseases, which is associated to a continue use of these treatments [Maker A V, et al., Ann Surg Oncol. 2005; 12(12):1005-16; Fadel F, et al., N Engl J Med. 2009; 361(2):211-2; Gogas H, et al., N Engl J Med. 2006; 354(7): 709-18. doi: 10.1056/NEJMoa053007].

Despite the diverse therapeutic approaches focusing on genetic and immunological targets, breast cancer is one of the most aggressive neoplasm, with a survival rate of 5 years in 22% of cases diagnosed with stage-IV [American Cancer Society, Breast Cancer. 2014: p. 1-127. Available in: http://www.cancer.org/acs/groups/cid/documents/webcontent/003090-pdf.pdf], suggesting that none of these therapies has been effective enough to increase the survival rate. Thus, it is necessary to find therapeutic options that allow us to increase the life expectancy of these patients. In this regard, the present invention shows the antitumor activity of the GK-1 peptide as a novel therapeutic approach that could increases the survival rate of patients with carcinoma.

GK-1 is an 18-aminoacid peptide (G-Y-Y-Y-P-S-D-P-N-T-F-Y-A-P-P-Y-S-A), identified and cloned from the KETc7 protein, which was first isolated from *Taenia crassiceps* cysticerci [Gevorkian G., et al., Immunol Lett, 1996. 49(3): p. 185-9]. The immunostimulating properties of GK-1 have been demonstrated in vitro by promoting T cell, macrophage, and dendritic cells activation, through the expression of CD80/86 and MHC-II, as well as the secretion of soluble pro-inflammatory factors like IFN-γ, TNF-α, and CCL2 [Segura-Velazquez R., et al., Clin Vaccine Immunol, 2009. 16(9): p. 1338-43]. Additionally, its capacity as the influenza vaccine adjuvant has been demonstrated in vivo, increasing the titer of specific IgG antibodies in a murine model with young and senile mice [Segura-Velazquez R., et al., Vaccine, 2006. 24(8): 1073-80; patent MX270782]. It should be noted that Segura et al., (2006) found that GK-1 promotes the infiltrate of mononuclear cells (lymphocytes and macrophages) to the lung parenchyma a few days after its subcutaneous administration, which could be related to the resolution of lung infections [Segura-Velazquez R., et al., Vaccine, 2006. 24(8):1073-80].

In the state of the art, Mexican patent 270782 presents the use of GK-1 as a drug substance, which improve the immune response elicited in mammals by the administration of different vaccine antigenic components, specifically influenza vaccine.

The US2014/0302085A1 patent describes FGK1, comprising GK-1 associated to the M13 filamentous phage as a phagemid, to boost the immunoprotective capacity of different vaccines, as well as to increase the immune response to control the establishment and development of various pathogens.

Additionally, GK-1 has been reported to increase the proliferation of TCD4+ and TCD8+ lymphocyte populations [Toledo A et al., Infection and Immun. 1999; 67 (5): 2522-30; Gladis F, et al., Clinical and Vaccine Immunology 2011; 18(7):1067-1076]. In this regard, several studies suggest a correlation of a higher density of CD3+CD8+T lymphocytes (cytotoxic) and CD3+CD45RO+ T lymphocytes (memory) infiltrated into the primary tumor with an increase in the survival of patients with types of neoplasms like melanoma, pancreas, breast, lung, and ovary cancer [Clemente C. G. et al., Cancer 1996, 77: 1303-1310; Fukunaga A. et al., Pancreas 2004; 28: e26-e31; Mahmoud S. M. et al., J. Clin. Oncol. 2011, 29:1949-1955; Oldford S. A. et al., Int. Immunol. 2006, 18: 1591-1602; Dieu-Nosjean M. C. et al., J. Clin. Oncol. 2008, 26: 4410-4417; and Zhang L., et al., N Engl J Med. 2003 Jan. 16;348(3):203-13].

Piñón et al., [Piñón-Zárate G. et al., J Immunol Res. 2014; 2014:158980. doi: 10.1155/2014/158980] described the use of GK-1 as an immunostimulant of dendritic cells (DCs) loaded with the MAGE antigen to be used as immunotherapy against murine melanoma, finding an increase in the activation of these DCs. This result offers an alternative for cancer treatment through the vaccination with DCs to induce effector T cells specific for tumors, aiming to reduce and control the tumor mass.

Additionally, Perez-Torres et al., [Perez-Torres A et al., Cancer Biother Radiopharm. 2013; 28(9):682-90] reported that GK-1 increased the mean survival, delayed tumor growth rate, and increased primary tumor necrosis in a mouse melanoma model. GK-1 administration along with surgical treatment increased mouse survival. While the potential of GK-1 to be included as a primary component in chemotherapy cocktails to treat this type of cancer has been suggested, we demonstrated that GK-1 is ineffective to stop metastasis in melanoma.

DESCRIPTION OF THE INVENTION

It is known that the tumor microenvironment is responsible for tumor progression and the response to antineoplastic treatment [Andrew E Place et al., Breast Cancer Research 2011, 13:227:1-11]. This microenvironment varies depending on the neoplasia type and the cell types present in the primary tumor. For instance, epithelial cancer cells can be found surrounded by pericytes, granulocytes, fibroblasts, macrophages, and endothelial cells in breast cancer primary tumors [Vesselina G. Cooke et al., Cancer Cell. 2012; 21(1): 66-81; Queen M M et al., Cancer Res. 2005; 65(19):8896-904; Mailer O et al., J Mammary Gland Biol Neoplasia 2010, 15:301-318]. This tumor microenvironment produces several soluble factors such as TNF-α, TGF-β1, EGF, and HIF-1α, all of which stimulate an epithelial-mesenchymal transition (EMT), promoting cancer progression, invasion, and metastasis [Wu Y et al., Cancer Cell, 2009,15(5):416-428; Oft M et al., Genes Dev. 1996; 10(19):2462-77; Lo H W et al., Cancer Res. 2007; 67(19):9066-76; Yang M H et al., Nat Cell Biol. 2008;10 (3):295-305].

According to the microenvironment induced by GK-1, the cancer type or cancer cell types that can be treated include but are not limited to carcinomas like basal cell carcinoma, squamous cell carcinoma, transitional cell carcinoma, and adenocarcinoma. Preferably, GK-1 is useful to manufacture a drug product to treat breast cancer in mammals and/or as an antitumor and antimetastatic agent in mammals.

GK-1 can be administered in single or multiple doses, intratumorally, parenterally, intranasally, intravenously in concentrations ranging from 10 μg to 500 μg. It can also be administered with a pharmaceutically appropriate vehicle, either as a monotherapy or as a component of therapeutic cocktails for cancer treatment including chemotherapy and radiotherapy.

As for the present invention, the term "vehicle" refers to any diluent or excipient administered along with GK-1. Vehicles can be sterile liquids such as diluted saline aqueous solutions, diluted dimethyl-sulfoxide (DMSO) solutions, xanthan gum, sodium methyl- or propyl-paraben, dextrose, and glycerol. Saline and DMSO solution are preferably used.

GK-1 can be administered in a pharmaceutically appropriate vehicle in concentrations up to 5 mg/mL when dissolved in isotonic saline solution (ISS) or concentrations higher than 5 mg/mL when dissolved in DMSO to a final application concentration of 0.05-2% in injectable water.

Example of Embodiment 1. Establishment of a Murine Cancer Model, Emulating Breast Cancer As used in the following Examples of Embodiment, GK-1 was synthesized under good manufacturing practices by USV, LTD, with a purity higher than 95%. The peptide was intravenously administered to mice at a dose of 0.5 mg/kg.

Four to six weeks-old female and male BALB/cAnN mice were used, with a weight range of 17-23 g for females and 20-27 g for males. All mice were maintained in pathogen-free conditions, as required by the Mexican Official Regulation NOM-062-ZOO-1999.

The 4T1 cell line (American Type Culture Collection, Manassas, Va.) was used to induce a neoplasia emulating breast cancer; according to the natural history of the disease, metastasis to lung should be observed [Aslakson C. J. et al., Cancer Res, 1992. 52(6): 1399-405; Mi Z et al., J Biol Chem, 2004. 279(45):46659-67]. The 4T1 cell line was cultured in RPMI medium (Gibco, Grand Island, N.Y.) supplemented with 10% of heat-inactivated fetal bovine serum, 10 U/mL of penicillin, and 100 μg/mL of streptomycin, at 37° C. under 95% relative humidity and 5% $CO_2$. Cultured cells were recovered by trypsinization (0.25% trypsin-0.53 mM EDTA) and washed three times with cold serum-free RPMI medium before subcutaneous implanting. About $1\times10^3$ 4T1 cells were subcutaneously injected in the right mammary gland in BALB/cAnN mice. Tumor induction was determined by the appearance of 1 mm×1 mm solid tumors (palpable tumor), between 18 and 20 days after cell implantation. Once the established tumors reached that size, mice were distributed into two groups: Group 1 (G1) was intravenously administered with a solution of 10 μg of GK-1 in 100 μL of ISS (corresponding to 0.5 mg/kg); Group 2 (G2) was administered with ISS (100 μL) by the same route. The administration was repeated weekly at different times.

All animals were weighed before treatment, and tumor growth was continuously recorded. Tumor volume was calculated according to the following formula [Carlsson G. et al., J Cancer Res Clin Oncol, 1983. 105(1): 20-23]: Volume $(mm^3) = \pi LW^2/6$, where L is the largest side and W is the smallest side.

At the day 39 after cell implanting, animals were euthanized in accordance with the guidelines in the United Kingdom Coordinating Committee on Cancer Research (UKCCCR). The primary tumor, spleen, lungs, liver, and brain were dissected. In total, five separate experiments were performed.

Example of Embodiment 2. Effect of GK-1 on Survival Rate in Mice with Breast Cancer To determine the survival rate in mice with breast cancer, $1 \times 10^3$ 4T1 cells were implanted to 40 BALB/cAnN mice as described in the Example of Embodiment 1; 10 males and 10 females were included in each group (G1 and G2). The administration schedule described in the Example of Embodiment 1 was repeated weekly after a solid tumor development, and for 62 days after cell implant.

The survival rate was established up to 62 days after cell implantation, at which time 100% of mice died. As shown in FIG. 1, GK-1-treated mice died from $44^{th}$ day up to the $62^{nd}$ day post-implantation, in contrast with untreated mice, which died from the $38^{th}$ day up to the $55^{th}$ day, which represents a statistically significant difference (P=0389).

Example of Embodiment 3. Effect of GK-1 on Tumor Growth Rate

As mentioned in the Example of Embodiment 1, once palpable tumors were developed in mice (G1: females $\bar{X}=6$, males $\bar{X}=4$; G2: females $\bar{X}=6$, males $\bar{X}=4$ per experiment), tumor volume was determined every third day for 39 days, with electronic Vernier. The results of the tumor growth rate are shown in FIG. 2. While GK-1-administered mice showed lower tumor volume than untreated mice, the difference was not statistically significant. Nevertheless, a significant reduction of 27.8% in tumor weight was found in GK-1-treated mice (1.04±0.70 g) with respect to untreated mice (1.44±0.69 g) (P=0.001) at the endpoint of the experiment (day 39), as shown in FIG. 3.

P-values for each experimental group in five independent experiments are shown in Table 1.

TABLE 1

| | Tumor weight | | |
|---|---|---|---|
| | G1 | G2 | P-value |
| Exp 1 | 0.825 ± 0.391 | 0.840 ± 0.371 | 0.999 |
| Exp 2 | 0.991 ± 0.507 | 1.022 ± 0.601 | 0.902 |
| Exp 3 | 1.150 ± 0.939 | 1.700 ± 0.282 | 0.666 |
| Exp 4 | 1.477 ± 0.889 | 1.700 ± 0.447 | 0.216 |
| Exp 5 | 0.587 ± 0.339 | 2.150 ± 0.988 | 0.008 |
| Total | 1.044 ± 0.697 | 1.439 ± 0.690 | 0.001 |

G1: GK-1-treated group
G2: Saline solution-treated group

Example of Embodiment 4. Effect of GK-1 on Tissue Death

A histological analysis was performed on primary tumors at day 39 post-implantation, to determine the percentage of zones with tissue death in mice from the Example of Embodiment 3. All tumors were manually sectioned and fixed in a 10% formaldehyde solution overnight at 4° C. Then, samples were included in paraffin and processed to obtain 4-μm slices; slices were stained with hematoxylin and eosin (H&E). The upper, middle, and deep tumor sections were analyzed through an Olympus Bx50 microscope equipped with a digital camera and using the Infinity Analyze software (v6.3.0).

The histopathological analysis of the superficial zone in primary tumors showed an increase in the area of necrotic-apoptotic cells in GK-1-treated mice, as shown in FIG. 4 (P=0.001). Additionally, cytological differences were observed between living cancer cells (large cells with a well-defined, basophilic nucleus with up to two nucleoli, surrounded by an eosinophilic cytoplasm) and dead cells (smaller cells, failing to show nucleus and cytoplasm staining due to an increase in diffuse eosinophilia) by H&E stain, as shown in FIG. 5. Likewise, apoptotic bodies were identified within or near necrotic zones.

Example of Embodiment 5. Antimetastatic Effect of GK-1

It is known that the metastasis sites in the 4T1 cell-induced breast cancer murine model are lungs, brain, liver, and bone [Aslakson C. J. et al., Cancer Res. 1992, 52(6): 1399-405; Mi Z. et al., J Biol Che. 2004; 279(45): 46659-67]. Therefore, to assess the antimetastatic effect of GK-1, lungs, liver, and brain from mice in G1 and G2 groups in the Example of Embodiment 3 were recovered and fixed with a 10% formaldehyde solution to macroscopically identify any metastatic focus on these organs. Under the studied conditions, macrometastasis were found only in lungs. FIG. 6 shows the different distributions of the number of metastatic foci in the G1 and G2 groups (P=0.0063); a higher proportion of foci within the 0-20 range was found in G1 mice (67%) than in G2 (38%).

As reported in various studies, about $1 \times 10^6$ cancer cells per tumor gram per day are released into the bloodstream [Butler T P et al., Cancer Res. 1975; 35(3):512-6]. Considering this, the antimetastatic effect of GK-1 could be related to an increase in the primary tumor tissue death, as seen in FIG. 4, which could limit the amount of living cells available to leave the primary tumor and enter the bloodstream, thus decreasing the possibility of establishing metastatic niches.

Example of Embodiment 6. Effect of GK-1 on Splenomegaly

Splenomegaly, a characteristic trait of the 4T1 murine model, is caused by granulocytes infiltrated (mostly immature GR-$1^{dim}$ cells) into the red pulp. Splenomegaly is correlated with the increase in primary tumor size [Thomas E. et al., Cancer Res. 1985, 45: 5840-5844; duPre S A et al., Exp Mol Pathol. 2007; 82(1):12-24; Kasugal, et al., Cancer. 2001; 92(9):2399-405]. Based on this, the weight of the spleen was determined in mice from both groups in the Example of Embodiment 3. The weight of the spleens from mice in the G1 and G2 groups increased significantly with respect to tumor-free mice, as shown in FIG. 7. Additionally, the correlation between spleen weight and primary tumor weight was analyzed; according to the results, G2 mice showed a positive correlation with a statistically significant slope of 1.01 (P=0094), in contrast with G1 mice, which show a slope lower than 0.57 (P=0.09), as shown in FIG. 8.

Example of Embodiment 7. Effect of GK-1 on Tumor Microenvironment

Lungs, liver, spleen, brain, and primary tumor were dissected from mice in the groups G1 and G2 of the Example of Embodiment 3, to determine the soluble factors present in the tumor microenvironment and in metastatic-associated organs; in order to obtained a protein extract, 5 mg of each tissue were weighed and placed in 300 µL of lysis buffer with protease inhibitors, then were homogenized. Finally, homogenates were centrifuged for 20 min at 13 000 rpm at 4° C., collecting the supernatants (protein extract). Additionally, serum was isolated from blood samples obtained from all mice. Serum and protein extract samples were processed through the Magpix Luminex system (xPonent software) to determine the concentration of cytokines, chemokines, and growth factors.

With respect to neoplasia-induced soluble factors, no differences were found in the cytokine profile in serum or liver samples from mice in the G1 and G2 groups of the Example of Embodiment 3. However, significant differences were found in lungs, brain, and in spleen. As seen in Table 2, the group G1 from the Example of Embodiment 3 shows a pro-inflammatory profile in spleen, associated to a significant increase of IL-12, IL-1α, CCL3, and CXCL9 concentrations. In contrast, the group G2 from the Example of Embodiment showed an increase in lung bFGF, CCL3, GM-CSF, TNF-α, CXCL9, and CCL2 concentrations with respect to G1 mice ($P<0.05$), as shown in Table 3. This profile could be related to the decrease in the number of lung macrometastasis in GK-1-treated mice (G1). Similarly, Table 4 shows an increase in bFGF, CCL2, and IL-5 concentration, along with a significant decrease in IL-4, IL-17, and IL-2 concentration in brains from G2 mice with respect to G1 mice. This decrease in chemokine and cytokine concentrations in G1 mice could modulate angiogenesis and the recruitment of macrophages associated to metastasis (MAM).

TABLE 2

Spleen cytokine, chemokine, and growth factor profile in the 4T1 mammary carcinoma murine model.

| | Spleen | |
|---|---|---|
| | G1 | G2 |
| bFGF | 2.30E+04 ± 3.54E+03 | 2.39E+04 ± 7.05E+03 |
| IL-12 | 8.06E+01 ± 3.61E+01 | * 2.40E+01 ± 1.30E+01 |
| IL-17 | 2.98E+00 ± 3.01E+00 | 3.41E+00 ± 2.43E+00 |
| CCL3 | 4.99E+01 ± 1.51E+01 | * 2.93E+01 ± 5.88E+00 |
| GM-CSF | 3.79E+01 ± 1.60E+01 | 2.97E+01 ± 1.40E+01 |
| CCL2 | 1.19E+01 ± 4.41E+00 | 7.74E+00 ± 4.21E+00 |
| IL-5 | 1.65E+02 ± 1.00E+02 | 1.18E+02 ± 3.92E+01 |
| IL-1α | 6.28E+02 ± 2.42E+02 | * 3.31E+02 ± 3.97E+01 |
| TNF-α | 1.00E+02 ± 2.46E+01 | 1.20E+02 ± 1.17E+02 |
| IL-2 | 6.65E+01 ± 1.05E+01 | 5.95E+01 ± 3.06E+00 |
| CXCL9 | 2.31E+04 ± 1.36E+04 | * 4.01E+03 ± 3.36E+03 |
| IL-4 | 7.03E+01 ± 9.56E+01 | 4.14E+01 ± 2.81E+01 |

TABLE 3

Lung cytokine, chemokine, and growth factor profile in the 4T1 mammary carcinoma murine model.

| | Lung | | | | |
|---|---|---|---|---|---|
| | G1 | | | G2 | |
| bFGF | 3.61E+03 | ± 1.73E+03 | * | 8.65E+03 | ± 3.93E+03 |
| IL-12 | 3.83E+00 | ± 1.11E+00 | | 1.90E+01 | ± 3.42E+01 |
| IL-17 | 6.22E+00 | ± 5.86E+00 | | 3.40E+00 | ± 2.01E+00 |
| CCL3 | 5.36E+01 | ± 5.69E+01 | * | 2.61E+02 | ± 3.54E+02 |
| GM-CSF | 4.06E+01 | ± 2.03E+01 | * | 9.30E+01 | ± 4.08E+01 |
| CCL2 | 4.71E+01 | ± 3.09E+01 | * | 1.33E+02 | ± 5.20E+01 |
| IL-5 | 2.06E+02 | ± 9.46E+01 | | 1.90E+02 | ± 9.12E+01 |
| IL-1α | 1.50E+02 | ± 6.33E+01 | | 2.29E+02 | ± 9.62E+01 |
| TNF-α | 3.21E+01 | ± 1.49E+01 | * | 5.91E+01 | ± 6.67E+00 |
| IL-2 | 6.28E+01 | ± 1.01E+01 | | 6.06E+01 | ± 1.36E+01 |
| CXCL9 | 3.88E+03 | ± 3.85E+03 | * | 2.03E+04 | ± 4.73E+03 |
| IL-4 | 1.49E+02 | ± 8.13E+01 | | 2.02E+02 | ± 1.05E+02 |

```
SEQ ID NO 1:
G-Y-Y-Y-P-S-D-P-N-T-F-Y-A-P-P-Y-S-A
```

TABLE 4

Brain cytokine, chemokine, and growth factor profile in the 4T1 mammary carcinoma murine model.

| | Brain | | | | |
|---|---|---|---|---|---|
| | G1 | | | G2 | |
| bFGF | 1.16E+04 | ± 1.54E+03 | * | 1.54E+04 | ± 2.95E+03 |
| IL-12 | 5.29E+00 | ± 0.00E+00 | | 4.79E+00 | ± 1.23E+00 |
| IL-17 | 8.06E+01 | ± 1.83E+01 | * | 5.35E+01 | ± 2.92E+01 |
| CCL3 | 1.40E+01 | ± 3.47E+00 | | 1.97E+01 | ± 4.08E+00 |
| GM-CSF | 2.53E+01 | ± 8.27E+00 | | 3.00E+01 | ± 1.08E+01 |
| CCL2 | 3.44E+00 | ± 2.06E+00 | * | 3.01E+01 | ± 2.05E+01 |
| IL-5 | 1.18E+02 | ± 2.19E+01 | * | 1.43E+02 | ± 5.17E+01 |
| IL-1α | 1.44E+01 | ± 3.44E+00 | | 1.83E+01 | ± 6.87E+00 |
| TNF-α | 1.26E+01 | ± 5.88E+00 | | 9.71E+00 | ± 3.92E+00 |
| IL-2 | 6.02E+01 | ± 7.11E+00 | * | 4.18E+01 | ± 1.19E+01 |
| CXCL9 | 1.44E+02 | ± 2.83E+01 | | 1.50E+02 | ± 3.42E+01 |
| IL-4 | 1.36E+02 | ± 5.13E+01 | * | 6.22E+01 | ± 2.60E+01 |

Data in Tables 2, 3, and 4 correspond to spleen, lung, and brain soluble factor concentrations expressed in pg/mg of protein. A random sample of 6 mice was taken from 5 independent experiments. * $P<0.05$.

The production of pro-inflammatory cytokines, growth factors, and chemokines by tumor and surrounding cells can promote neoplasia progression, by facilitating carcinogenesis programs, inducing a sustained cell proliferation rate, inhibiting apoptosis, and stimulating angiogenesis [Wolczyk D et al., Cell Oncol (Dordr) 2016; Lorusso G et al., Histochem Cell Biol. 2008 130(6):1091-103. doi: 10.1007/s00418-008-0530-8]. With respect to angiogenesis, a decrease in bFGF and GM-CSF levels in GK-1-treated mice (G1 group) with respect to the G2 group could be modulating a diminished response in the development of new blood vessels. In this regard, bFGF is a tumorigenic factor, whose production can induce angiogenesis, cell proliferation, and tumor cell survival [Turner N et al., Nat Rev Cancer. 2010; 10(2):116-29. doi: 10.1038/nrc2780].

With respect to MAM recruitment, the lower lung CCL2 and CCL3 concentrations induced in GK-1-treated mice could be decreasing the response associated to the migration and infiltration of monocytes, T cells memory, and NK cells, thus helping to control the metastasis to lungs [Qian B Z, et al., Nature. 2011; 475(7355):222-5; Kitamura T, et al., J Exp Med. 2015; 212(7):1043-59. doi: 10.1084/jem.20141836].

As shown in Table 4, GK-1-treated mice exhibited lower brain bFGF and CCL2 concentrations, which could be associated to the absence of macrometastatic foci in brain. The role of bFGF in angiogenesis has been reported in gliomas (brain tumors), altering NK cell recruitment and adhesion to blood vessels by deregulating endothelial adhesion molecules [Takahashi J A et al., Proc Natl Acad Sci USA. 1990; 87(15):5710-4; Melder R J et al., Nature Medicine 1996; 2(9):992-7].

Example of Embodiment 8. Effect of GK-1 on Melanoma Metastasis

The B16 melanoma model is a lung metastasis model widely used for therapy evaluation. While the term "lung metastasis" is used to characterize this type of model, technically each lung nodule is a primary tumor.

To determine the survival rate of mice with melanoma and demonstrate the antitumor effect of GK-1, $2\times10^4$ cells of the B16-F10 line were intravenously injected to C57BL/6 mice (n=29). Once the tumor is established (16 days after B16-F10 cells were implanted), mice were separated into four groups: One group was administered with a 0.10 µg/µL GK-1 solution in DMSO (0.05%); another group was administered with 0.10 µg/µL GK-1 solution in ISS; a third group received 100 µL of DMSO (0.05%); and a fourth group was administered with 100 µL of ISS; treatments were applied intravenously in all cases. Treatments were repeated weekly after a palpable tumor appeared and for 32 days after cell implantation.

As shown in FIG. 9, mice administered with GK-1 dissolved in DMSO showed a survival rate of 25%, while those mice that received ISS and the GK-1 dissolved in ISS showed a survival rate of 42.86% and 57.14%, respectively. Finally, the highest survival percentage was observed in the group administered with DMSO (71.43%).

In order to establish the antitumor effect of GK-1, lungs were dissected from mice in all experimental groups at the day 32 post-implantation, and were fixed in a 10% formaldehyde solution to macroscopically determine the number of tumor foci developed. As shown in FIG. 10, no statistically significant differences were found in the number of tumor foci developed in lungs from mice receiving the different treatments.

To evaluate the antimetastatic effect of GK-1 in melanoma, $2\times10^4$ cells of the B16-F10 line were intravenously injected to C57BL/6 mice (n=40; 20 females and 20 males). At day 16 post-implantation, mice were separated into two groups: The G1 group (10 males and 10 females) was intravenously administered with 10 µg of GK-1 dissolved in 100 µL of ISS; the G2 group (10 males, 10 females) was intravenously administered with 100 µL of ISS. Treatments were repeated weekly for 32 days after cell implantation. As shown in Table 5, the number of lung tumor foci developed in the G1 and G2 groups are not significantly differences, which clearly demonstrates that GK-1 is ineffective to stop metastasis in melanoma.

TABLE 5

Number of tumors developed in the murine lung melanoma model

| G1 | | | G2 | | |
|---|---|---|---|---|---|
| Tumors | Lung | Distant | Tumors | Lung | Distant |
| Males | | | | | |
| 77.0 ± 37.6 | 8/10 | 0/10 | 69.5 ± 45.7 | 6/9 | 1/10 |
| Females | | | | | |
| 62.9 ± 48.1 | 8/10 | 1/10 | 62.8 ± 48.3 | 7/10 | 2/10 |

Data are reported as mean±standard deviation.
Data labeled as Distant refers to those tumors developed at sites other than the lungs (liver, brain, and intestine).
No statistically significant differences were observed between the experimental groups.

---

SEQUENCE LISTING

Figure 1:
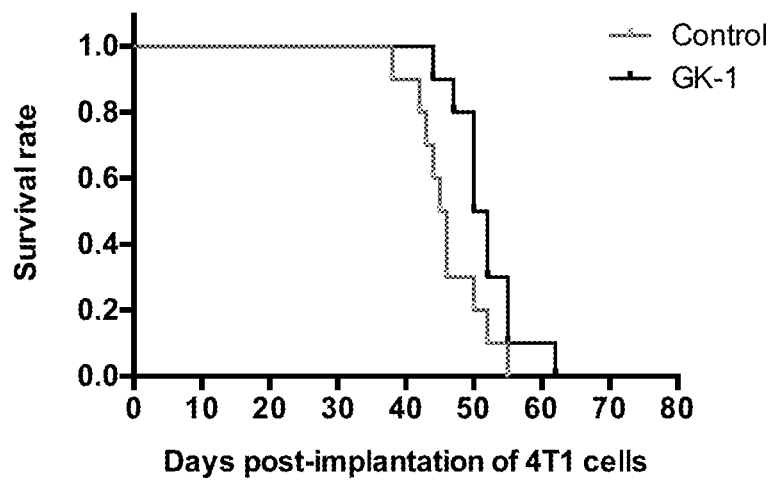
FIG. 1 shows a survival rate after 60 days post-implantation in a 4T1 mammary carcinoma murine model. Through the Kaplan-Meyer survival curve, it was determined that treatment with GK-1 (black line) significantly increased survival with respect to saline-treated mice (grey line) (P=0.038, log-rank test).
Figure 2:
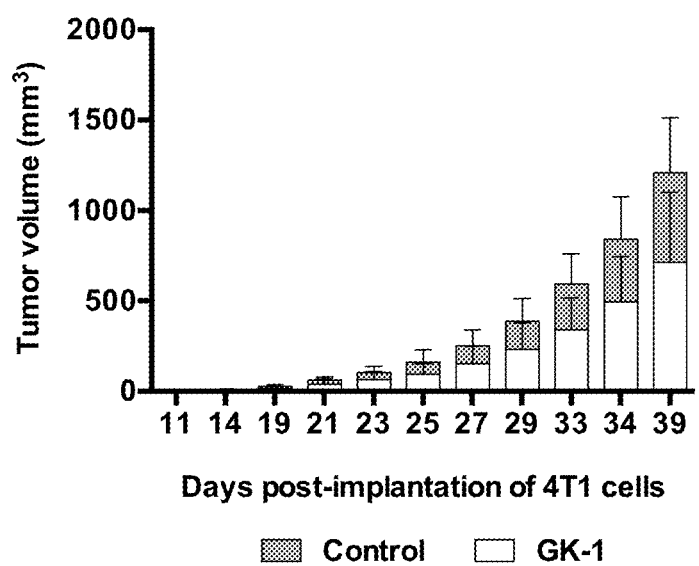
FIG. 2 shows tumor volume rate ($mm^3$) measured in each mouse from the G1 (GK-1) and G2 (control) groups. Data are reported as mean±SD for GK-1-treated mice (G1: white bars) and saline-treated mice (G2: grey bars).
Figure 3:
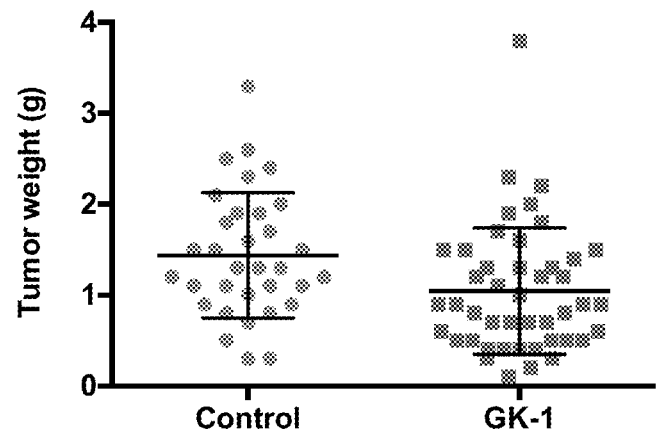
FIG. 3 shows tumor weight measured at 39 days' post-implantation of 4T1 cells in mice from the G1 and G2 groups. Mice were sacrificed and tumors were dissected and weighed. The graph shows the individual values (n=45 for G1; n=33 for G2) and mean weight ±SD.
Figure 4:
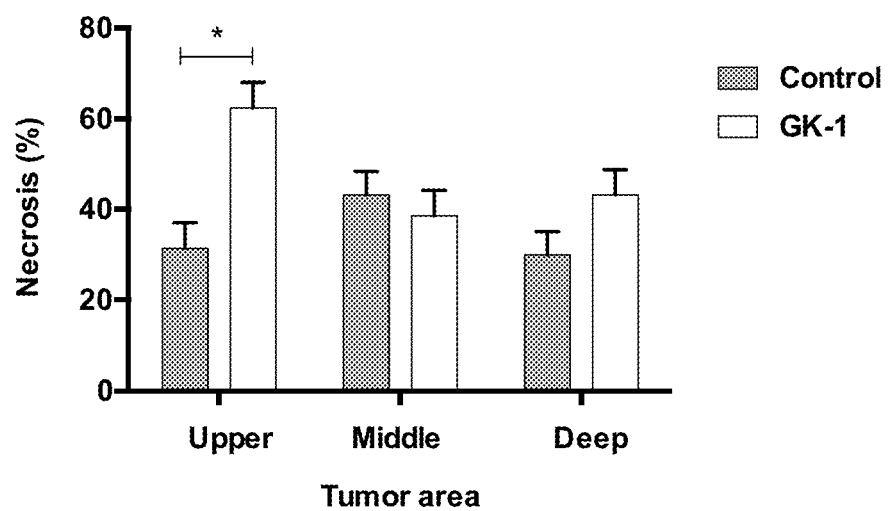
FIG. 4 shows the percent of necro-apoptotic areas in superficial, middle, and deep sections of primary tumors obtained 39 days after implanting 4T1 cells in mice from the G1 (white bars) and G2 (grey bars) groups, which was assessed by hematoxylin and eosin stain (H&E). Data are reported as mean±SD.
Figure 5:
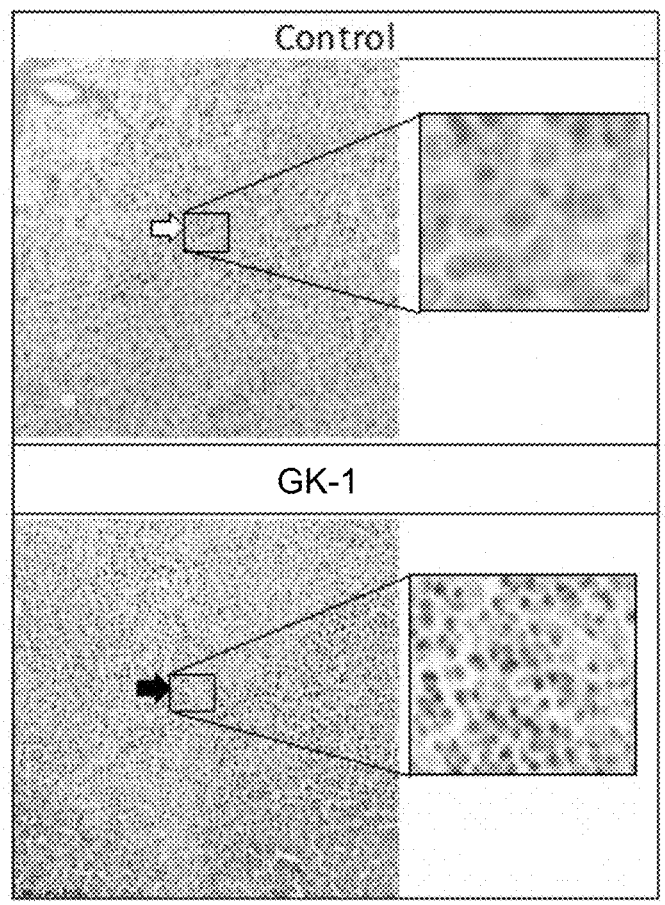
FIG. 5 shows the histopathological analysis in serial sections by light microscopy HE×10 in primary tumors from GK-1-treated mice (G1 group) and ISS-treated mice (G2 group). Histopathological analysis of primary tumors shows clear cytological differences between living cancer cells (white arrow) (large cells with a well-defined, basophilic nucleus with up to two nucleoli, surrounded by an eosinophilic cytoplasm) with respect to necrotic cells (smaller cells with diffuse nucleus and cytoplasm due to an increase in diffuse eosinophilia). Additionally, apoptotic bodies were observed within or near necrotic zones.
Figure 6:
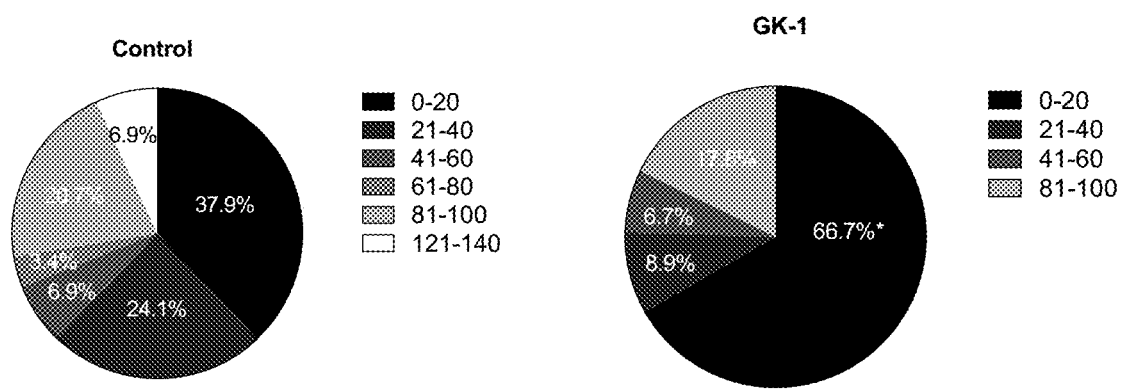
FIG. 6 shows the distribution in the number of metastatic foci in the lungs from mice of the G1 and G2 groups. Values correspond to the cumulated percentage of mice that developed 0-20, 21-40, 41-60, 61-80, 81-100, 101-120, and 121-140 lung metastatic foci. Data represent the results of five experiments.
Figure 7:
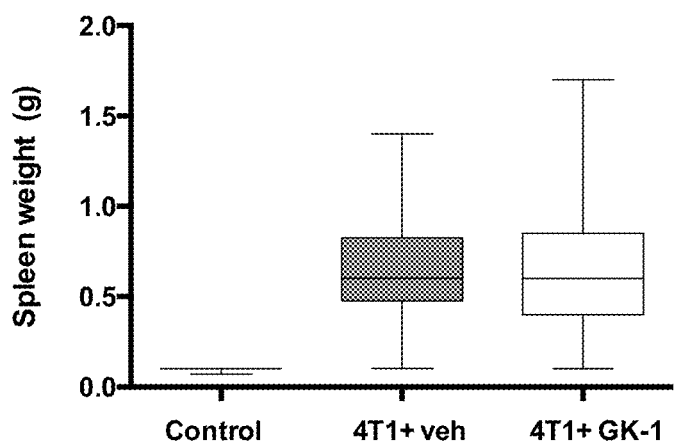
FIG. 7 shows the weight of spleens from tumor-free mice (control) and either tumor-affected, GK-1-treated mice (4T1+ GK-1) or tumor-affected, ISS-treated mice (4T1+ veh). Data are reported as mean weight, and whiskers represent the maximum and minimum values. Data represent the results of five experiments.
Figure 8:
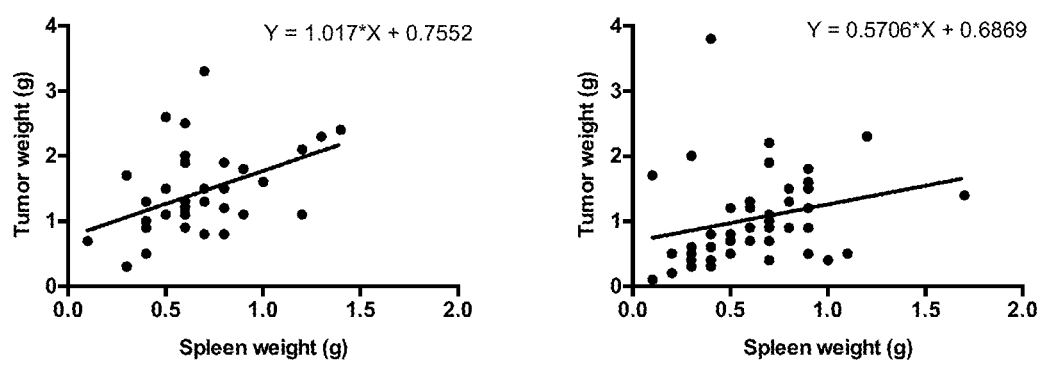
FIG. 8 shows plots A and B, depicting the correlation between primary tumor weight and spleen weight in tumor-bearing mice, either administered with ISS (A) or GK-1 (B). Data represent the results of five experiments.
Figure 9:
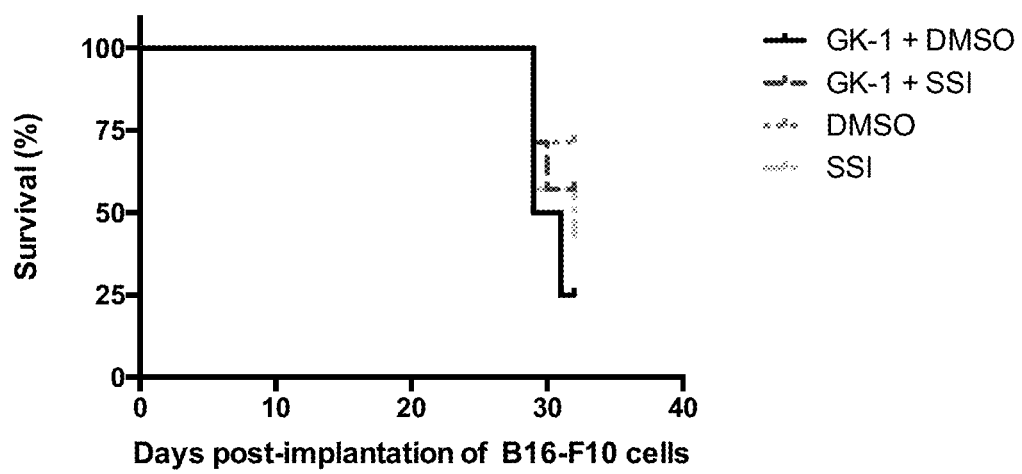
FIG. 9 shows the survival rate in a melanoma model, 32 days after B16-F10 cells implantation to mice treated with GK-1 dissolved in DMSO (black line), GK-1 dissolved in ISS (dark grey, dashed line) and the vehicles DMSO and ISS alone (light grey, dotted and dashed lines, respectively).
Figure 10:
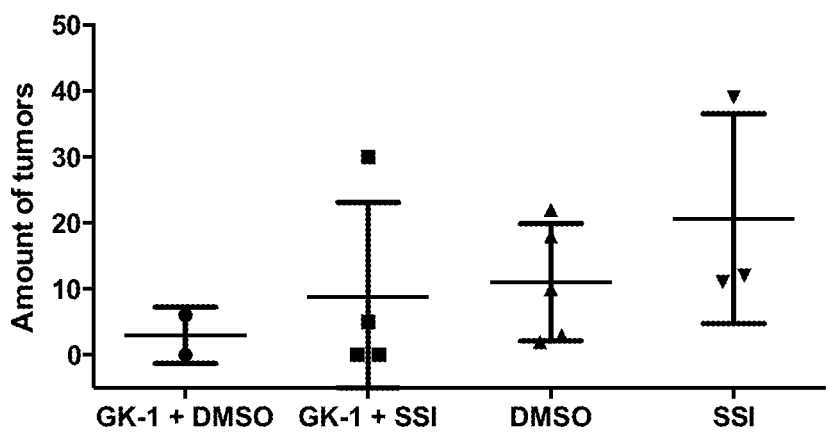
FIG. 10 shows the individual data and the mean±SD of lung tumor foci developed in mice treated with GK-1 dissolved in DMSO (circle), GK-1 dissolved in ISS (square) and the vehicles DMSO and ISS alone (triangles) in a melanoma murine model.

```
<160> NUMBER OF SEQ ID NOS: 1

<210> SEQ ID NO 1
<211> LENGTH: 18
<212> TYPE: PRT
<213> ORGANISM: Unknown
<220> FEATURE:
<223> OTHER INFORMATION: tapeworm

<400> SEQUENCE: 1

Gly Tyr Tyr Tyr Pro Ser Asp Pro Asn Thr Phe Tyr Ala Pro Pro Tyr
1               5                   10                  15

Ser Ala
```

---

What is claimed is:

1. A method of treating mammary cancer in a mammal comprising:
    administering an effective amount of an antitumor and antimetatstatic agent comprising a peptide having an amino acid sequence G-Y-Y-Y-P-S-D-P-N-T-F-Y-A-P-P-Y-S-A (SEQ ID NO:1) to mammary cancer cells in the mammal; and
    reducing mammary cancer cell growth in the mammal by administering the antitumor and antimetatstatic agent comprising the peptide having the amino acid sequence G-Y-Y-Y-P-S-D-P-N-T-F-Y-A-P-P-Y-S-A (SEQ ID NO:1) to the mammal, wherein: the mammary cancer is breast cancer.

2. The method of claim 1, wherein SEQ ID NO:1 is administered as a single or multiple dose(s) intratumorally, parenterally, intranasally, or intravenously.

3. The method of claim 1, wherein SEQ ID NO:1 is administered as a single antitumor agent.

4. The method of claim 1, wherein SEQ ID NO:1 is administered as a therapeutic cocktail for cancer treatment.

5. The method of claim 1, wherein the therapeutic cocktail further comprises chemotherapy and/or radiotherapy.

6. The method of claim 1, wherein SEQ ID NO:1 is administered in concentrations ranging from 10 µg to 500 µg.

7. The method of claim 1, wherein the antitumor and antimetastatic agent configured to treat breast cancer.

8. The method of claim 1, wherein the antitumor and antimetatstatic agent is administered in a pharmaceutically appropriate vehicle, the pharmaceutically appropriate vehicle is a sterile liquid selected from the group consisting of water or aqueous saline solutions, diluted DMSO solutions, xanthan gum, sodium methyl- or propyl-paraben, dextrose, and glycerol.

9. The method of claim 1, wherein the antitumor and antimetastatic agent is administered in concentrations up to 5 mg/mL when an isotonic saline solution (ISS) is used as the vehicle, or in concentrations higher than 5 mg/mL when diluted DMSO is used as the vehicle, to a final concentration of 0.05-2% in injectable water.

* * * * *